United States Patent [19]

Blaser et al.

[11] Patent Number: 5,198,569
[45] Date of Patent: Mar. 30, 1993

[54] PROCESS FOR THE PREPARATION OF OPTICALLY ACTIVE ALIPHATIC HYDROXYCARBOXYLIC ACIDS

[75] Inventors: Hans-Ulrich Blaser, Ettingen, Switzerland; Ulrich Pittelkow, Rheinfelden, Fed. Rep. of Germany; Felix Spindler, Starrkirch-Wil, all of Switzerland

[73] Assignee: Ciba-Geigy Corporation, Ardsley, N.Y.

[21] Appl. No.: 758,927

[22] Filed: Sep. 11, 1991

[30] Foreign Application Priority Data

Nov. 2, 1990 [CH] Switzerland .................. 3490/90

[51] Int. Cl.$^5$ .............................................. C07C 69/76
[52] U.S. Cl. ............................... 560/60; 560/16; 560/29; 560/56; 560/59; 560/147; 560/148; 560/160; 560/161; 560/179; 560/180; 560/187
[58] Field of Search ............. 560/60, 179, 16, 29, 560/56, 59, 147, 148, 160, 161, 180, 187

[56] References Cited

PUBLICATIONS

R. Williams, Synthesis of Optically Active α–Amino Acids, Pergamon Press 1990, p. 196.
Homogeneous Catalysis with Metal Phosphine Complexes, B. Heil et al, Plenum Press N.Y. 1983 pp. 324–332.
Wissenschaftliche Zeitschrift THLM 27(6), pp. 746–750.
Pat. Abstr. of Jap. C2, No. 140, p. 3095 C78, Kokai No. 53–105420, Oct. 18, 1978.
Pat. Abstr. of Jap. C2, No. 140, p. 3095 C78, Kokai No. 53–105421, Oct. 18, 1978.

*Primary Examiner*—Paul J. Killos
*Attorney, Agent, or Firm*—Kevin T. Mansfield; Edward McC. Roberts

[57] ABSTRACT

The asymmetric hydrogenation of aliphatic α-keto esters in the presence of rhodium catalysts which contain as chiral ligand a diphosphine of formula IV $$(R_3)_2P-Q-P(R_3)_2 \qquad (IV)$$

wherein $R_3$ is phenyl, $C_1$–$C_6$alkylphenyl or $C_1$–$C_6$alkoxyphenyl, and Q is [2,2,1]-bicyloheptan-1,2-ylene or [2,2,1]-bicyclohept-4,5-en-1,2-ylene, gives the corresponding (R)- or(S)-α-hydroxycarboxylic acid esters in high rates of chemical conversion and in high enantiomer excesses.

15 Claims, No Drawings

PROCESS FOR THE PREPARATION OF OPTICALLY ACTIVE ALIPHATIC HYDROXYCARBOXYLIC ACIDS

The present invention relates to a process for the preparation of enantiomeric aliphatic α-hydroxycarboxylic acid esters by the catalytic hydrogenation of prochiral aliphatic α-ketocarboxylic acid esters in the presence of rhodium complexes with a chiral diphosphine ligand which forms a 5-membered ring together with the rhodium atom.

The enantioselective homogeneous hydrogenation of prochiral α-ketocarboxylic acid esters in the presence of rhodium complexes containing chiral diphosphine ligands is known and described by B. Heil et al. in Homogeneous Catalysis with Metal Phosphine Complexes, Plenum Press, New York, pp. 324-332 (1983) or by B. Heil in Wissenschaftliche Zeitschrift THLM 27, pp. 746-750 (1985). In these publications attention is expressly drawn to the fact that chiral bidentate bis(diphenylphosphine) ligands which form a 5-membered ring with the rhodium atom are not suitable for the reduction of ketones.

It has now been found that it is possible to attain high chemical conversions and high enantioselectivities with rhodium catalysts which contain such a 5-membered ring by using aliphatic α-ketocarboxylic acid esters as ketones and a rhodium catalyst containing a bicyclic 1,2-diphosphine.

Specifically, the invention relates to a process for the preparation of optically active α-hydroxycarboxylic acid esters of formula I $$R\text{—}C^*H(OH)CO_2R_1 \qquad (I)$$

wherein R is linear or branched $C_1$-$C_{12}$alkyl which is unsubstituted or substituted by halogen, —OH, —$CO_2R_1$, —$CO_2N(R_2)_2$, $(R_2)_2N$—, $C_1$-$C_6$alkoxy or $C_1$-$C_6$alkylthio, $C_4$-$C_8$cycloalkyl, $C_4$-$C_8$cycloalkoxy, $C_4$-$C_8$cycloalkylthio, phenyl, naphthyl, phenoxy, naphthoxy, phenylthio or naphthylthio, and the substituents cycloalkyl, cycloalkoxy, cycloalkylthio, phenyl, naphthyl, phenoxy, naphthoxy, phenylthio and naphthylthio are themselves unsubstituted or substituted by halogen, —OH, —$CO_2R_1$, —$CO_2N(R_2)_2$, $(R_2)_2N$—, $C_1$-$C_6$alkoxy or $C_1$-$C_6$alkylthio; $R_1$ is $C_1$-$C_6$alkyl, phenyl or benzyl; both substituents $R_2$ are each independently of the other $C_1$-$C_6$alkyl, phenyl, benzyl or, when taken together, are tetramethylene, pentamethylene, 3-oxa-1,5-pentylene or N-($C_1$-$C_6$alkyl)-3-aza-1,5-pentylene, and * denotes the predominantly R- or S-configuration, by hydrogenation of α-keto esters of formula II $$R\text{—}C(=O)CO_2R_1 \qquad (II),$$

wherein R and $R_1$ are as defined above, in the absence or presence of an inert solvent at a pressure of 0.1 to 15 MPa and in the temperature range from −20° C. to 100° C., and also in the presence of catalytic amounts of a rhodium complex with chiral diphosphine ligands, which rhodium complex has the formula III $$[XRhYZ] \qquad (III),$$

wherein X is two $C_2$-$C_{12}$olefins or a $C_5$-$C_{12}$diene, Z is Cl, Br or I, and Y is a chiral diphosphine of formula IV $$(R_3)_2P\text{—}Q\text{—}P(R_3)_2 \qquad (IV)$$

wherein $R_3$ is phenyl, $C_1$-$C_6$alkylphenyl or $C_1$-$C_6$alkoxyphenyl, and Q is [2,2,1]-bicyloheptan-1,2-ylene or [2,2,1]-bicyclohept-4,5-en-1,2-ylene.

R as alkyl preferably contains 1 to 6 and, most preferably, 1 to 4 carbon atoms. Alkyl is typically methyl, ethyl, and the isomers of propyl, butyl, pentyl, hexyl, heptyl, octyl, nonyl, decyl, undecyl and dodecyl.

The radical R and the substituents cyloalkyl, cycloalkoxy, cycloalkylthio, phenyl, naphthyl, phenoxy, naphthoxy, phenylthio and naphthylthio may be substituted by one or more, preferably by one to three, of the same or different substituents. Suitable substituents of R and the cited substituents are, in addition to —OH, as halogen, —F, —Cl and —Br;
as alkoxy, preferably $C_1$-$C_4$alkoxy, such as methoxy, ethoxy, n- or isopropoxy, n-, iso- or tert-butoxy, pentoxy and hexoxy,
as alkylthio, preferably $C_1$-$C_4$alkylthio, such as methylthio and ethylthio,
as cycloalkyl, preferably cyclopentyl and cyclohexyl,
as cycloalkoxy, preferably cyclopentoxy and cyclohexoxy,
as cycloalkylthio, preferably cyclopentylthio and cyclohexylthio,
as —$CO_2R_1$, preferably —$CO_2CH_3$ and —$CO_2C_2H_5$,
as —$CO_2N(R_2)_2$, preferably —$CO_2N(CH_3)_2$ and —$CO_2N(C_2H_5)_2$, and,
as $(R_2)_2N$—, preferably methylamino, ethylamino, dimethylamino and diethylamino.

$R_1$ and $R_2$ as alkyl may preferably be methyl, ethyl, n- or isopropyl, n-, iso- or tert-butyl, pentyl or hexyl.

In a preferred embodiment of the invention, R is linear or branched $C_1$-$C_4$alkyl and, more particularly, $C_1$-$C_2$alkyl, which is unsubstituted or substituted by —F, —Cl, —Br, —OH, —CN, —$CO_2R_1$, —$CO_2N(R_2)_2$, $(R_2)_2N$—, $C_1$-$C_4$alkoxy, $C_4$-$C_8$cycloalkyl, phenyl, phenoxy or phenylthio, and the substituents cycloalkyl, phenyl, phenoxy and phenylthio are themselves unsubstituted or substituted by —F, —Cl, —Br, —OH, —CN, —$CO_2R_1$, —$CO_2N(R_2)_2$, $(R_2)_2N$— or $C_1$-$C_4$alkoxy; $R_1$ is $C_1$-$C_4$alkyl, phenyl or benzyl; both substituents $R_2$ are each independently of the other H, $C_1$-$C_4$alkyl, phenyl or benzyl, or, when taken together, are tetramethylene, pentamethylene, 3-oxa-1,5-pentylene or N-($C_1$-$C_4$alkyl)-3-aza-1,5-pentylene. Most preferably R is $C_1$-$C_4$alkyl, benzyl or β-phenylethyl.

In a further preferred embodiment of the invention, $R_1$ is preferably $C_1$-$C_4$alkyl, phenyl or benzyl and both substituents $R_2$ are each independently of the other preferably methyl, ethyl, n-propyl or n-butyl or, when taken together, are tetramethylene or pentamethylene.

X as an olefin preferably contains 2 to 6 and, most preferably, 2 to 4, carbon atoms. Ethylene is especially preferred. Further examples are propene and 1-butene. X as diene preferably contains 5 to 8 carbon atoms and may be an open-chain or mono- or bicyclic diene. Both olefin groups of the diene are preferably linked through one or two $CH_2$ groups. Illustrative examples of such groups are 1,3-pentadiene, cyclopentadiene, 1,4-hexadiene, 1,4-cyclohexadiene, 1,4- or 1,5-heptadiene, 1,4- or 1,5-cycloheptadiene, 1,4- or 1,5-octadiene, 1,4- or 1,5-cyclooctadiene, norbornadiene. Preferably X is 2-ethylene, 1,4-hexadiene, 1,5-cyclooctadiene or norbornadiene.

The preferred meaning of Z in formula III is Cl or Br.

In formula IV the preferred meaning of $R_3$ is phenyl, methylphenyl, dimethylphenyl, methoxyphenyl or dimethoxyphenyl. Most preferably $R_3$ is phenyl.

The diphosphine of formula IV is most preferably 1,2-bis(diphenylphosphino)-[2,2,1]-bicyclohept-4,5-ene, which is either in the R- or S-form. This diphosphine is also termed (+)-NORPHOS or (−)-NORPHOS.

The compounds of formula II are known and some are commercially available, or they can be prepared by analogous processes. The compounds of formula III are known, for example from EP-A-0 302 021. These rhodium catalysts are usually prepared in situ before the reaction and used direct. It is preferred to use the rhodium catalysts in amounts of 0.01 to 5, most preferably, 0.05 to 2 mol %, based on the compounds of formula II. The molar ratio of compounds of formula II to compounds of formula III can be from 10 000 to 20, preferably from 2000 to 50.

The process of this invention is preferably carried out in the temperature range from 0° C. to 80° C. and preferably under a hydrogen pressure of 2 to 10 MPa.

The reaction can be carried out without or in the presence of an inert solvent. Typical examples of suitable solvents, which may be used alone or as mixtures, are alcohols such as methanol, ethanol, propanol, butanol, pentanol and hexanol. Suitable solvents for mixtures are aliphatic and aromatic hydrocarbons, such as pentane, hexane, cyclohexane, methylcyclohexane, benzene, toluene and xylene; ethers, such as diethyl ether, diethylene glycol dimethyl ether, ethylene glycol dimethyl ether, tetrahydrofuran and dioxane; esters and lactones, such as ethyl acetate, butyrolactone or valerolactone; carboxamides and lactams, such as dimethyl formamide, dimethyl acetamide and N-methylpyrrolidone. Preferred mixtures are those of alcohols and aromatic hydrocarbons, typically methanol/benzene or methanol/toluene. The preferred solvent is methanol alone or a mixture of methanol with benzene or toluene.

A particularly preferred embodiment of the process of the invention comprises using ethyl α-ketopropionate or ethyl pyruvate as substrate, an alkanol as solvent, and carrying out the hydrogenation under a pressure of 2 to 10 MPa and in the temperature range from 0° to 80° C.

The compounds of formula I are useful intermediates for the synthesis of biologically active compounds, especially for use in the agrochemical and pharmaceutical fields. When R in formula I is β-phenylethyl, it is possible to prepare therefrom ACE inhibitors (q.v. EP-A-0 206 993). The compounds of formula I are generally intermediates for the preparation of optically active α-amino acids which are used typically in peptide synthesis (q.v. R. M. Williams, Synthesis of Optically Active α-Amino Acids, Pergamon Press, New York, page 196 (1990).

The following Examples illustrate the invention in more detail.

EXAMPLE 1

1.35 g (11.64 mmol) of methyl pyruvate (substrate) are charged to a 50 ml steel autoclave which is thereafter flushed 5 times with argon. A catalyst solution consisting of 53.3 mg (0.116 mmol) of [Rh(norbornadiene)Cl]$_2$, 117.8 mg (0.255 mmol) of (+)-NORPHOS and 10 ml each of methanol and toluene is then added using a steel capillary. The molar ratio of substrate/catalyst is 100. Then hydrogen is introduced in three cycles under a pressure of 1 MPa and the hydrogen pressure is adjusted to 2 MPa. The reaction mixture is stirred for 13 hours at 25° C. and subsequently transferred to a flask and the solvent is removed on a rotary evaporator. The chemical conversion is 100%, affording α-hydroxypropionic acid in an enantiomer excess (ee) of 89%.

Determination of the conversion: gas chromatography with Varian ® 3700, OV 101 column, 2 m, T: 50° C. isotherm.

Determination of the optical yield: gas chromatography after derivatisation of the crude product with isopropyl isocyanate; chirasil-L-Val column, 50 m, T: 150° C., isotherm.

EXAMPLE 2

The general procedure of Example 1 is repeated and the reaction conditions are modified as follows:

4.0 g of ethyl pyruvate, molar ratio of substrate/catalyst 800, pressure 10 MPa, temperature 35° C., reaction time 17 hours. The conversion is 100%, ee: 80%.

EXAMPLE 3

The general procedure of Example 1 is repeated and the reaction conditions are modified as follows:

2.4 g of ethyl 1-phenyl-α-ketobutyrate, molar ratio of substrate/catalyst 50, solvent methanol, pressure 2 MPa, temperature 22° C., reaction time 2 hours. The conversion is 80%, ee: 95.6%.

EXAMPLE 4

The general procedure of Example 3 is repeated and the reaction conditions are modified as follows:

1.0 g of ethyl 1-phenyl-α-ketobutyrate, molar ratio of substrate/catalyst 200, pressure 10 MPa, temperature 30° C., reaction time 20 hours. The conversion is 100%, ee: 91.4%.

EXAMPLES 5-9

The general procedure of Example 1 is repeated and the reaction conditions are modified as follows:

2.17 g (10.5 mmol) of ethyl pyruvate, 22 mg (0.048 mmol) of [Rh(norbornadiene)Cl]$_2$, 50 mg (0.11 mmol) of (+)-NORPHOS, 25° C., 10 MPa, 30 ml of solvent.

Further particulars are given in the following table.

| Example | Solvent | Hydrogenation time (hours) | Conversion (%) | ee* |
|---|---|---|---|---|
| 5 | isopropanol | 17 | 98.5 | 85 |
| 6 | n-butanol | 17 | 79 | 84 |
| 7 | tetrahydrofuran/methanol (1:1) | 19.5 | 85 | 90.5 |
| 8 | ethanol/ethyl acetate (1:1) | 20 | 88 | 80.5 |
| 9 | methanol/ethyl acetate (1:1) | 22.5 | 99 | 89 |

*configuration S.

EXAMPLE 10

The general procedure of Example 1 is repeated and the reaction conditions are modified as follows:

4 g of ethyl 4-phenyl-α-ketobutyrate, ratio of substrate/catalyst 200, solvent ethanol, pressure 10 MPa, temperature 30° C., hydrogenation time 18 hours. The conversion is 98%, ee: 87% (S).

What is claimed is:

1. A process for the preparation of an optically active α-hydroxycarboxylic acid ester of formula I $$R-C^*H(OH)CO_2R_1 \qquad (I),$$

wherein R is linear or branched $C_1$–$C_{12}$alkyl which is unsubstituted or substituted by halogen, —OH, —$CO_2R_1$, —$CO_2N(R_2)_2$, $(R_2)_2N$—, $C_1$–$C_6$alkoxy or $C_1$–$C_6$alkylthio, $C_4$–$C_8$cycloalkyl, $C_4$–$C_8$cycloalkoxy, $C_4$–$C_8$cycloalkylthio, phenyl, naphthyl, phenoxy, naphthoxy, phenylthio or naphthylthio, and the substituents cycloakyl, cycloalkoxy, cycloalkylthio, phenyl, naphthyl, phenoxy, naphthoxy, phenylthio and naphthylthio are themselves unsubstituted or substituted by halogen, —OH, —$CO_2R_1$, —$CO_2N(R_2)_2$, $(R_2)_2N$—, $C_1$–$C_6$alkoxy or $C_1$–$C_6$alkylthio; $R_1$ is $C_1$–$C_6$alkyl, phenyl or benzyl; both substituents $R_2$ are each independently of the other $C_1$–$C_6$alkyl, phenyl, benzyl or, when taken together, are tetramethylene, pentamethylene, 3-oxa-1,5-pentylene or N-($C_1$–$C_6$alkyl)-3-aza-1,5-pentylene, and * denotes the predominantly R- or S-configuration, by hydrogenation of an α-ketocarboxylic acid ester of formula II $$R-C(=O)CO_2R_1 \qquad (II),$$

wherein R and $R_1$ are as defined above, in the absence or presence of an inert solvent at a pressure of 0.1 to 15 MPa and in the temperature range from −20° C. to 100° C., and also in the presence of catalytic amounts of a rhodium complex with chiral diphosphine ligands, which rhodium complex has the formula III $$[XRhYZ] \qquad (III),$$

wherein X is two $C_2$–$C_{12}$olefins or a $C_5$–$C_{12}$diene, Z is Cl, Br or I, and Y is a chiral diphosphine of formula IV $$(R_3)_2P-Q-P(R_3)_2 \qquad (IV)$$

wherein $R_3$ is phenyl, $C_1$–$C_6$alkylphenyl or $C_1$–$C_6$alkoxyphenyl, and Q is [2,2,1]-bicyloheptan-1,2-ylene or [2,2,1]-bicyclohept-4,5-en-1,2-ylene.

2. A process according to claim 1, wherein the reaction temperature is in the range from 0° to 80° C.

3. A process according to claim 1, which is carried out in the pressure range from 2 to 10 MPa.

4. A process according to claim 1, wherein R in formula I is $C_1$–$C_6$alkyl which is unsubstituted or substituted as defined in claim 1.

5. A process according to claim 1, wherein $R_1$ is $C_1$–$C_4$alkyl, phenyl or benzyl.

6. A process according to claim 1, wherein both substituents $R_2$ are each independently of the other methyl, ethyl, n-propyl or n-butyl or, when taken together, are tetramethylene or pentamethylene.

7. A process according to claim 1, wherein R is linear or branched $C_1$–$C_4$alkyl which is unsubstituted or substituted by —F, —Cl, —Br, —OH, —CN, —$CO_2R_1$, —$CO_2N(R_2)_2$, $(R_2)_2N$—, $C_1$–$C_4$alkoxy, $C_4$–$C_8$cycloalkyl, phenyl, phenoxy or phenylthio, and the substituents cycloalkyl, phenyl, phenoxy and phenylthio are themselves unsubstituted or substituted by —F, —Cl, —Br, —OH, —CN, —$CO_2R_1$, —$CO_2N(R_2)_2$, $(R_2)_2N$— or $C_1$–$C_4$alkoxy; $R_1$ is $C_1$–$C_4$alkyl, phenyl or benzyl; both substituents $R_2$ are each independently of the other $C_1$–$C_4$alkyl, phenyl or benzyl, or, when taken together, are tetramethylene, pentamethylene, 3-oxa-1,5-pentylene or N-($C_1$–$C_4$alkyl)-3-aza-1,5-pentylene.

8. A process according to claim 1, wherein X in formula III is a $C_2$–$C_6$olefin or an open-chain or mono- or bicyclic $C_5$–$C_8$diene.

9. A process according to claim 1, wherein X is 2-ethylene, 1,4-hexadiene, 1,5-cyclooctadiene or norbornadiene.

10. A process according to claim 1, wherein Z in formula III is Cl or Br.

11. A process according to claim 1, wherein $R_3$ in formula IV is phenyl, methylphenyl, dimethylphenyl, methoxyphenyl or dimethoxyphenyl.

12. A process according to claim 1, wherein the diphosphine of formula IV is 1,2-bis(diphenylphosphino)-[2,2,1]-bicyclohept-4,5-ene, which is either in the R- or S-form.

13. A process according to claim 1, wherein the rhodium catalyst is used in an amount of 0.01 to 5 mol %, based on the compounds of formula II.

14. A process according to claim 1, wherein the solvent is methanol by itself or a mixture of methanol with benzene or toluene.

15. A process according to claim 1, which comprises using an ethyl α-ketopropionate or ethyl pyruvate as substrate, an alkanol as solvent, and carrying out the hydrogenation under a pressure of 2 to 10 MPa and in the temperature range from 0° to 80° C.

* * * * *